Figure 1:
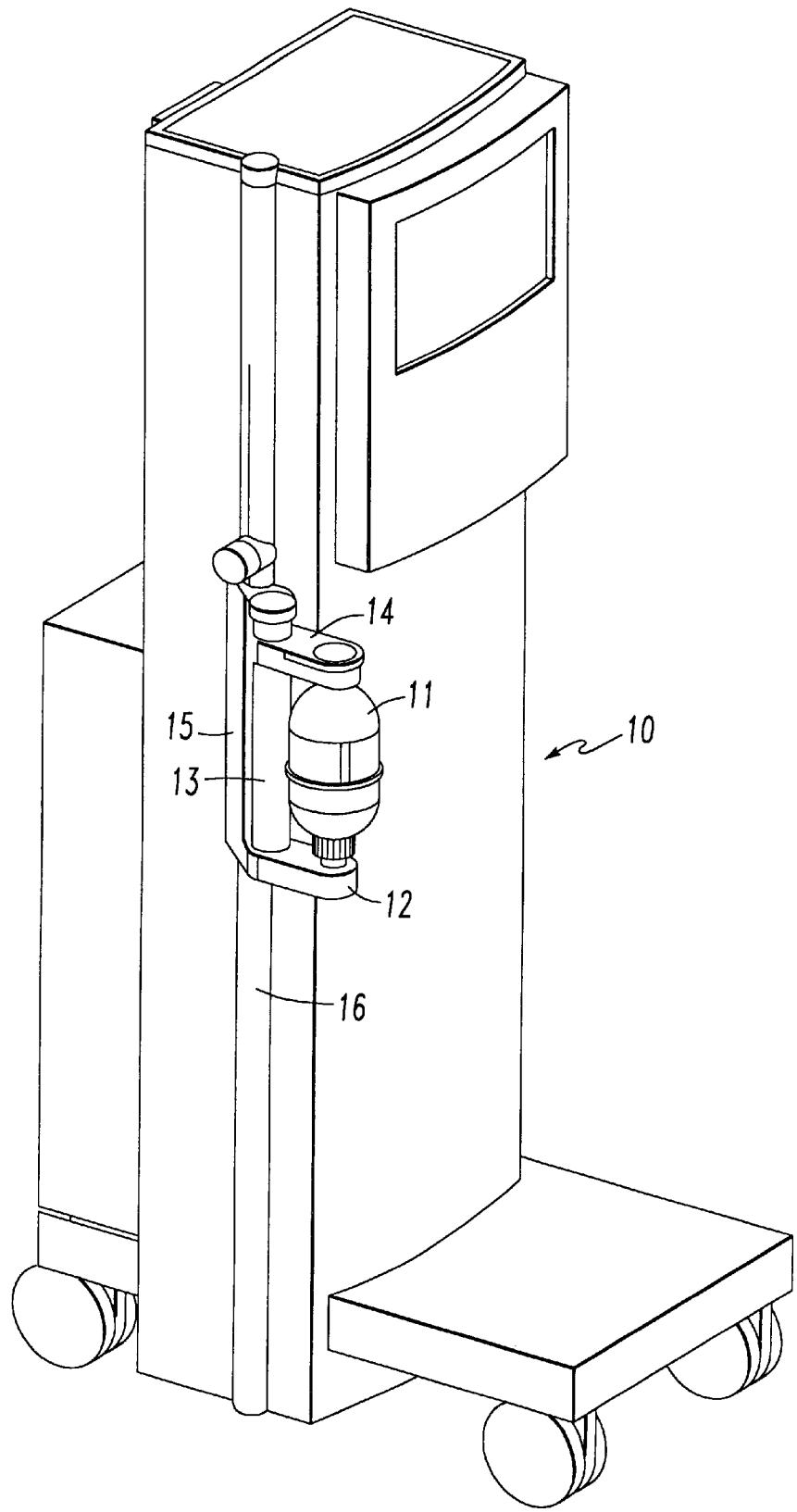

United States Patent
Carlsson et al.

[11] Patent Number: 6,000,567
[45] Date of Patent: Dec. 14, 1999

[54] DEVICE IN A POWDER CARTRIDGE FOR A DIALYSIS MACHINE

[75] Inventors: Per-Olov Carlsson; Bjorn Gillerfalk, both of Ronneby; Thore Falkvall, Helsingborg, all of Sweden

[73] Assignee: Althin Medical AB, Ronnneby, Sweden

[21] Appl. No.: 08/981,756

[22] PCT Filed: Jul. 3, 1996

[86] PCT No.: PCT/SE96/00896

§ 371 Date: Apr. 24, 1998

§ 102(e) Date: Apr. 24, 1998

[87] PCT Pub. No.: WO97/02055

PCT Pub. Date: Jan. 23, 1997

[30] Foreign Application Priority Data

Jul. 3, 1995 [SE] Sweden .................................. 9502396

[51] Int. Cl.[6] .................................................. B65D 47/10
[52] U.S. Cl. ........................ 215/252; 215/250; 222/521; 222/541
[58] Field of Search .................................. 215/252, 249, 215/251, 256; 222/541, 521

[56] References Cited

U.S. PATENT DOCUMENTS

| | | |
|---|---|---|
| 2,151,826 | 3/1939 | Andersen . |
| 4,458,817 | 7/1984 | Guala ........................................ 215/252 |
| 4,569,456 | 2/1986 | Weiler et al. ............................ 215/252 |
| 4,940,154 | 7/1990 | Vollmar .................................... 215/252 |
| 5,088,613 | 2/1992 | Dutt et al. ................................ 215/252 |
| 5,588,502 | 12/1996 | Sander et al. ............................ 215/252 |

FOREIGN PATENT DOCUMENTS

| | | |
|---|---|---|
| 0008190 | 2/1980 | European Pat. Off. . |
| 0296103 | 12/1988 | European Pat. Off. . |
| 3543825 | 6/1986 | Germany . |
| 4217352 | 4/1993 | Germany . |

Primary Examiner—Joseph M. Moy
Attorney, Agent, or Firm—James Ray & Associates

[57] ABSTRACT

A device in a powder cartridge (11) for a dialysis machine (10), having an externally threaded neck (21) which can be closed by means of a screw cap (26). In this screw cap there is provided a normally closed valve (36) which can be adjusted to open position at insertion of the powder cartridge into the dialysis machine. The end wall (28) of the screw cap and the neck (21) have mutually cooperating means (25, 33) which are adapted, when the cap is screwed on, to be interengaged for preventing unscrewing of the cap, and the end wall (28) has a break connection with the rest of the screw cap to allow unscrewing of the cap only under breaking of the connection (29) between the end wall and the rest of the cap in order to separate the end wall from the cap.

13 Claims, 16 Drawing Sheets

DEVICE IN A POWDER CARTRIDGE FOR A DIALYSIS MACHINE

A device in a powder cartridge for a dialysis machine The invention relates to a powder cartridge for a dialysis machine, having a screw cap and an externally threaded neck to which said screw cap can be applied.

A powder cartridge of this type is disclosed in DE-A4 217 352.

EP-B1 0 278 100 describes a dialysis system wherein the dialysis liquid is prepared at the site of use from a powder (sodium bicarbonate) which is supplied in a closed container—cartridge—which is inserted into a holder on the machine and is connected to an inlet for water and an outlet for the concentrated solution of the powder, which is obtained when water flows through the cartridge and dissolves the powder. This liquid concentrate then is added in an accurately measured amount to a water flow in the machine for obtaining dialysis liquid having the required concentration.

In a dialysis machine available on the market, which operates with this system, Gambro AK 100, the cartridge is inserted between two yaws pivotally mounted on a vertical wall of the machine one above the other, one of these yaws having an inlet for water and the other an outlet for the liquid concentrate obtained by dissolving the powder in the cartridge when water is allowed to flow through the cartridge. Then, the inlet and the outlet are connected to hollow studs which are provided at the ends of the cartridge. The connection takes place by penetrating membranes which are provided on the hollow studs and close these studs. The upper yaw is swung upwards when the cartridge is to be located between the yaws or is to be removed from this position after the powder in the cartridge having been consumed, but the yaws can also be swung towards said wall of the machine, the upper yaw downwards and the lower yaw upwards, in order that the inlet and the outlet, respectively, shall be connected with two connection pieces on the wall which are dimensioned in the same manner as the hollow studs on the cartridge. Between these connection pieces there is provided a short circuit conduit so that liquid can flow from one yaw to the other via the short-circuit conduit without passing through a cartridge positioned between the yaws. This short-circuit connection is used also when the machine between two dialysis treatments following one upon the other has to be rinsed and disinfected by circulating a flow of disinfection liquid through the machine.

After a dialysis treatment there is always left some liquid in the cartridge. When the cartridge after completed dialysis treatment is removed from the prior art dialysis machine it accordingly cannot be avoided that this liquid flows out onto the lower yaw and soils not only this yaw but also parts of the machine located below said yaw, and the floor where the machine is located.

The purpose of the invention is to eliminate this drawback which is most annoying for the personnel performing the dialysis treatment, by providing a powder cartridge wherein liquid remaining in the cartridge will be maintained therein when the cartridge is removed from the dialysis machine, and can be discharged into a sink or the like.

It is a further purpose of the invention to construct the screw cap screwed onto the outlet of the powder cartridge after the powder having been filled into the cartridge, in such a way that the screw cap after the cartridge having been emptied cannot be used again for closing the cartridge in order that the cartridge cannot be refilled at the site of use with the risks connected therewith: wrong dosage of the powder, refilling with powder of a wrong composition, contamination of the interior space of the cartridge, etc.

The purposes mentioned above are achieved by the powder cartridge according to the invention having obtained the characterizing features of claim 1.

Figure 2:
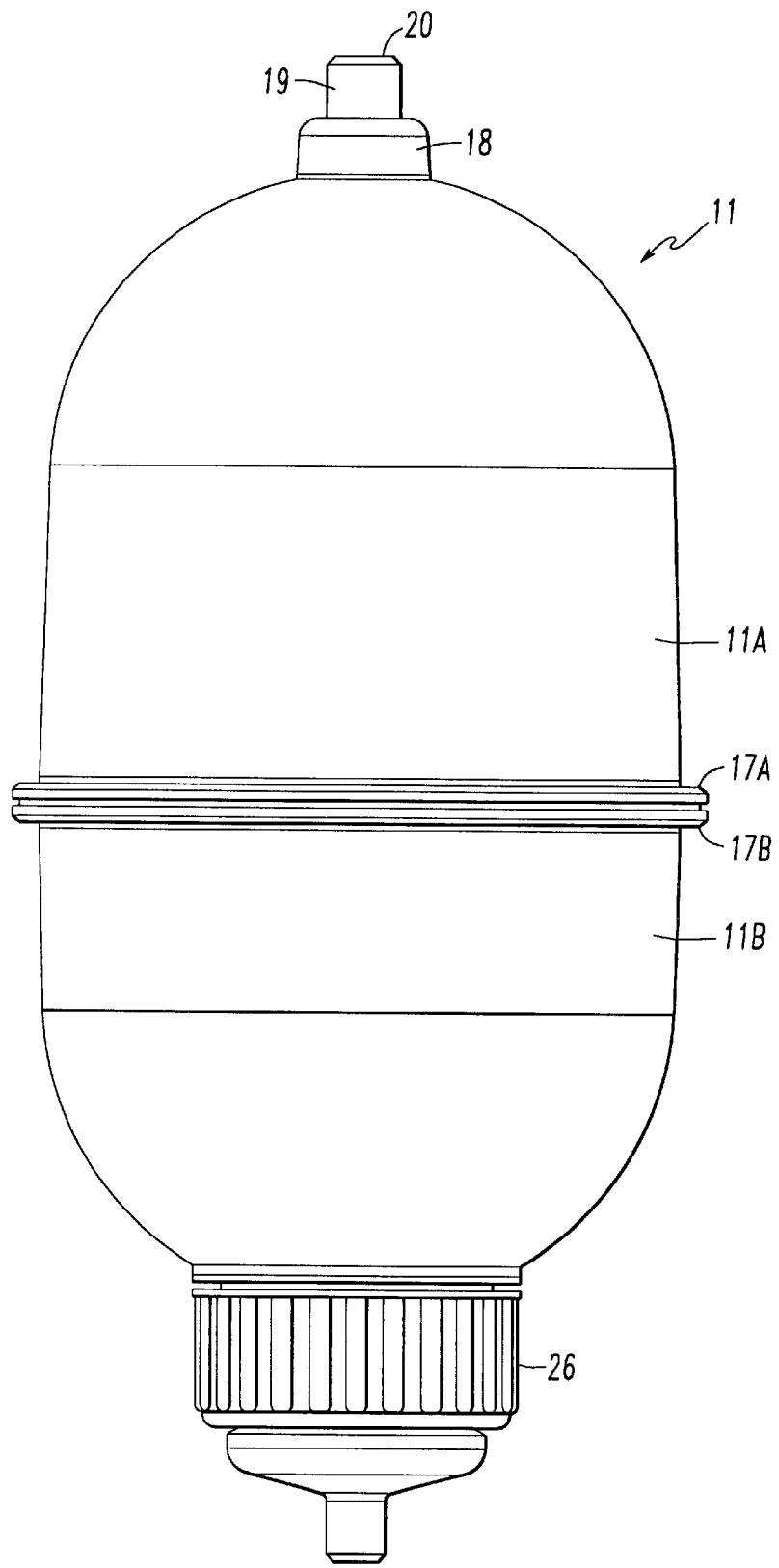
Figure 3:
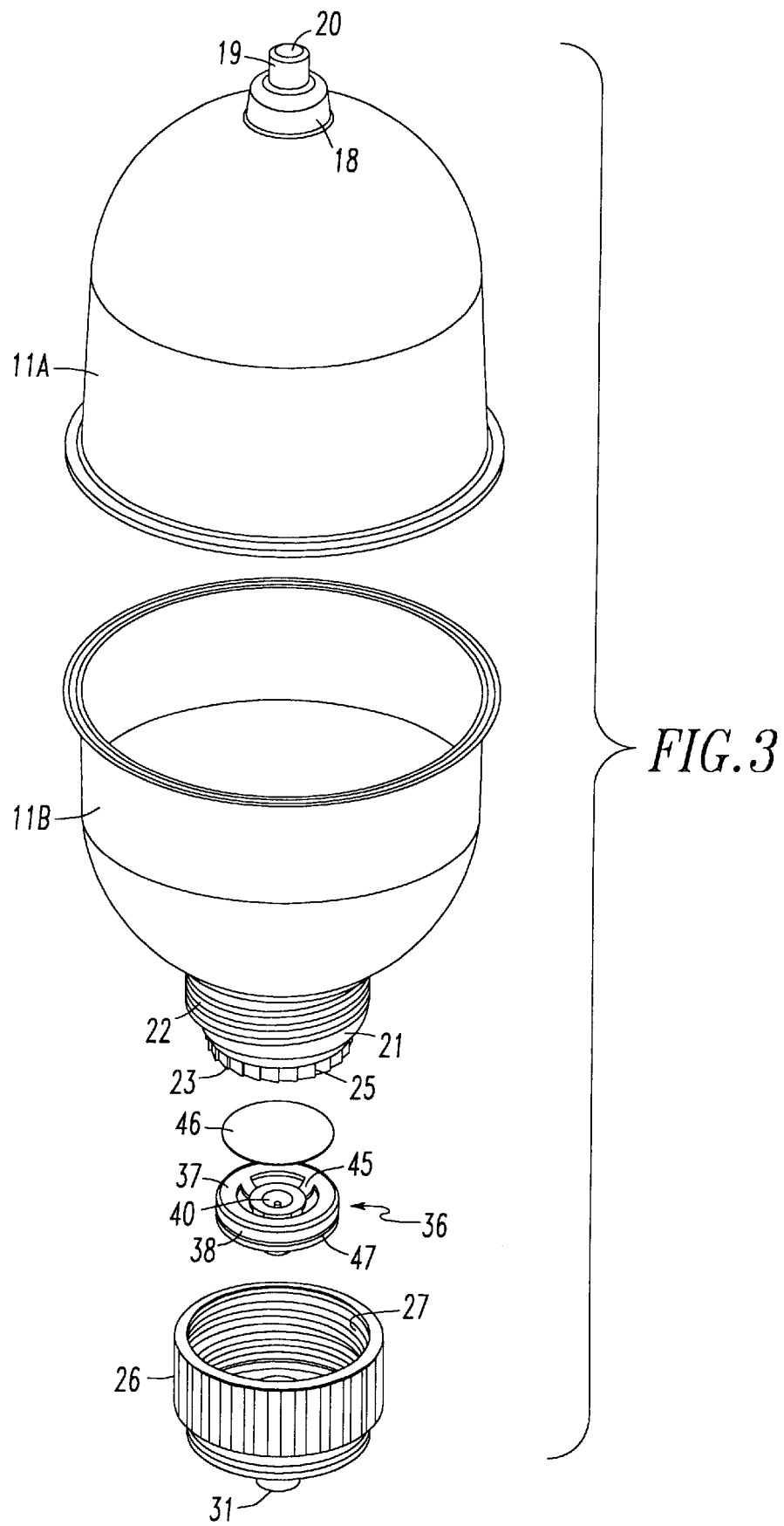
Figure 4:
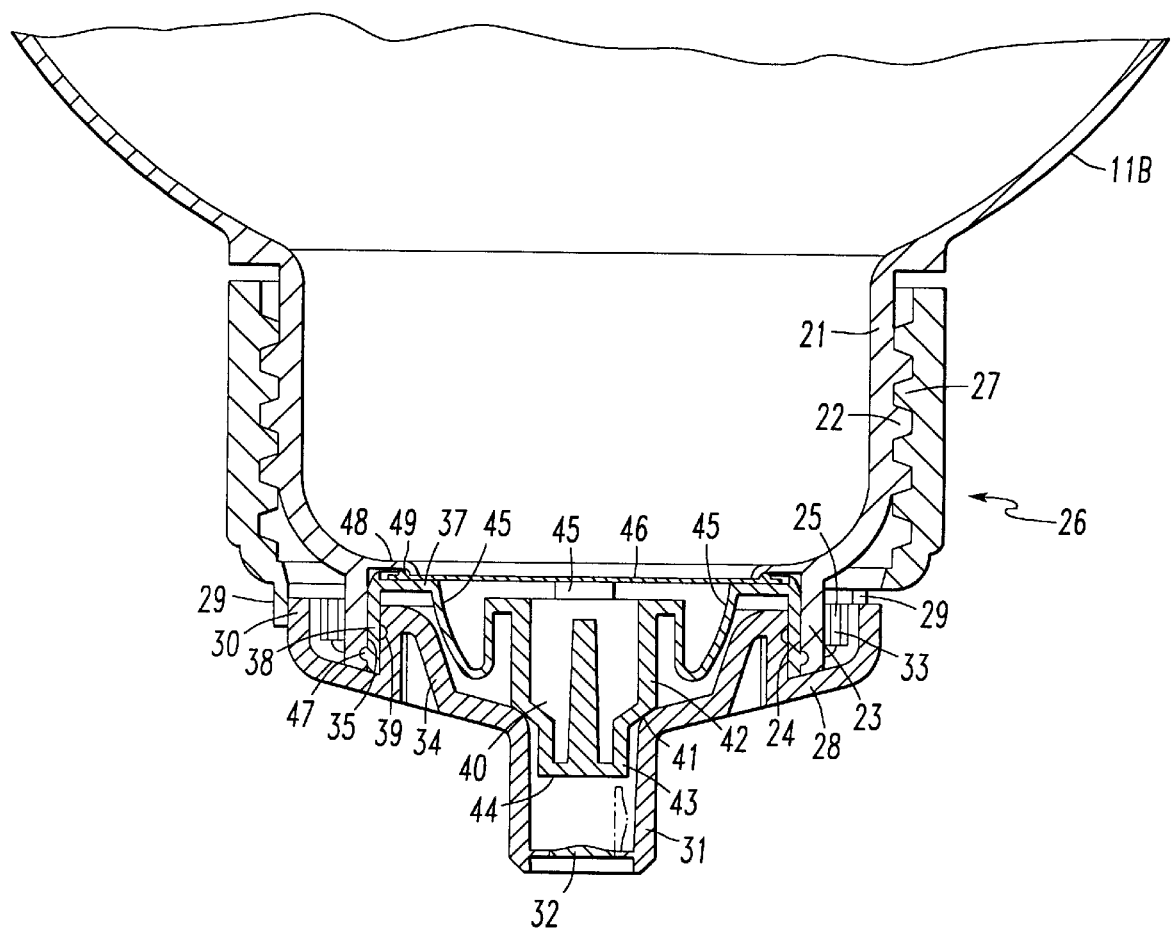
Figure 5:
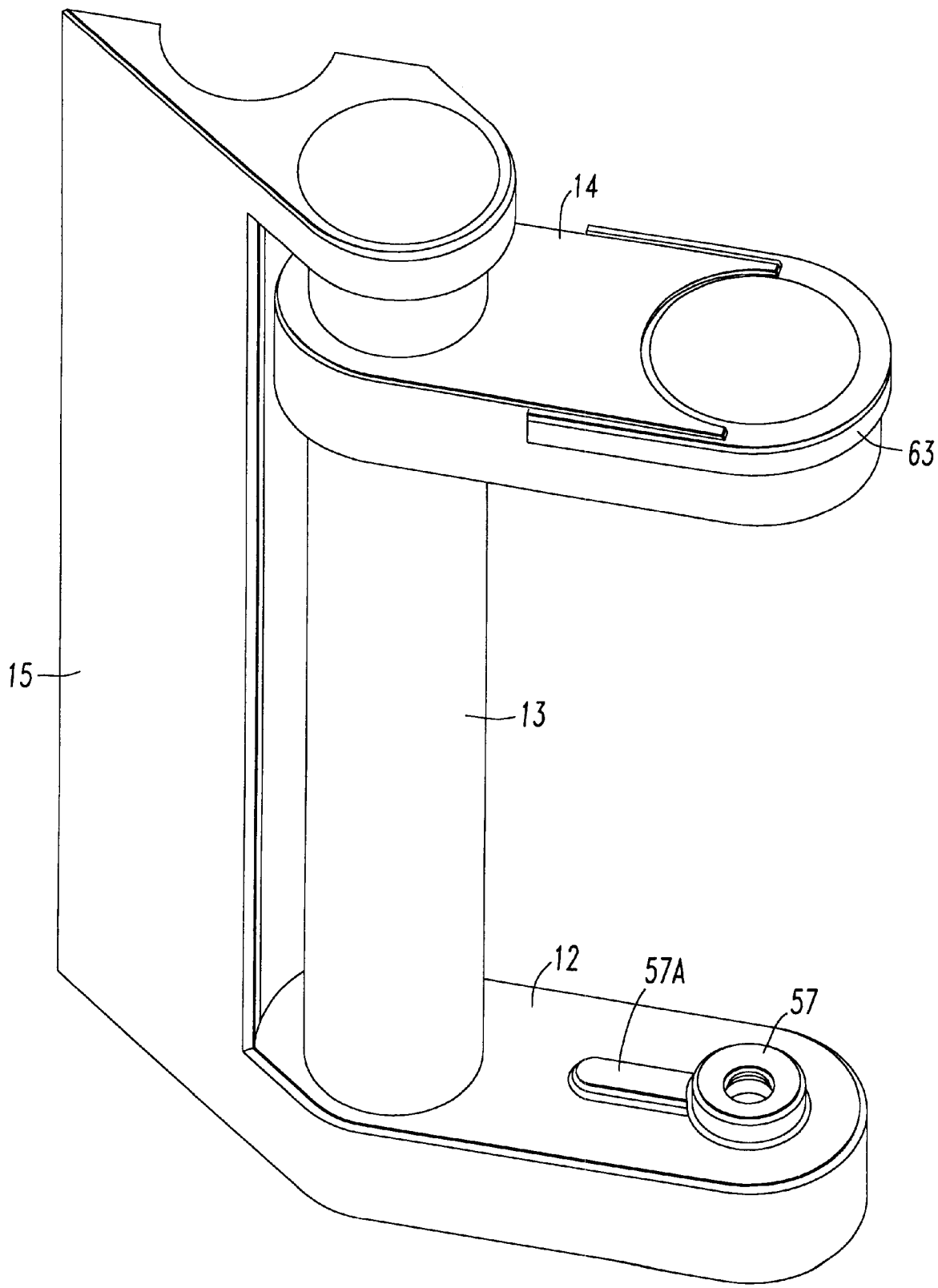
Figure 6:
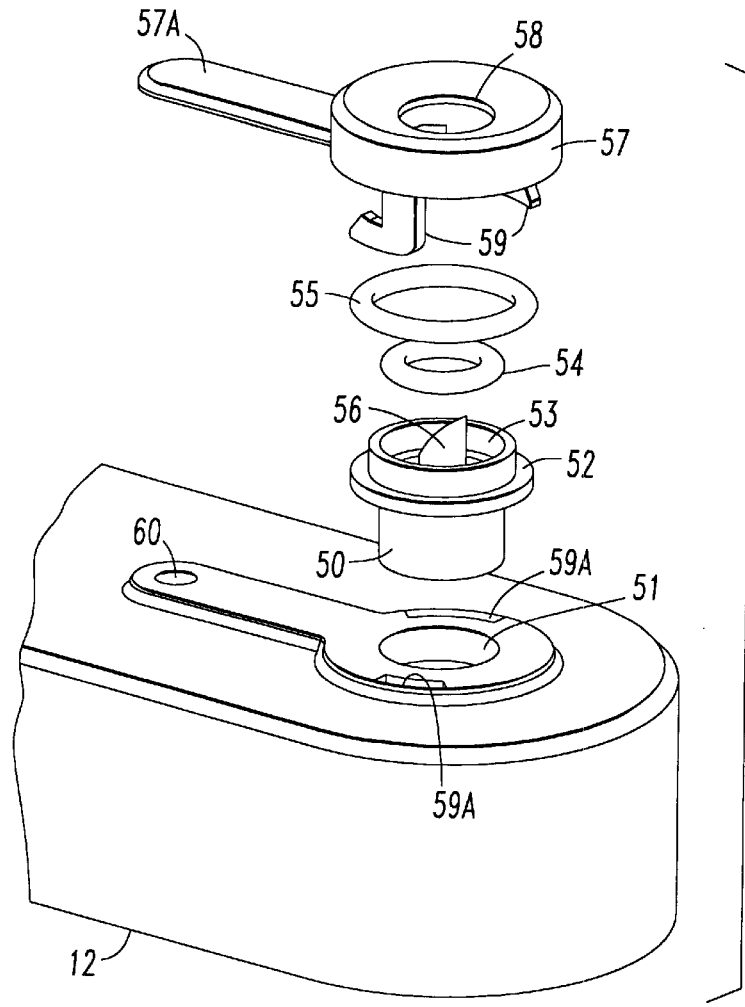
Figure 7:
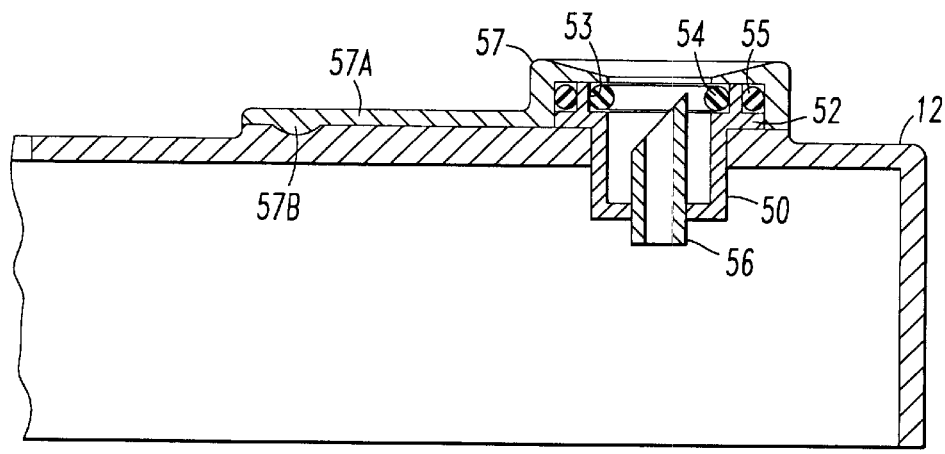
Figure 8:
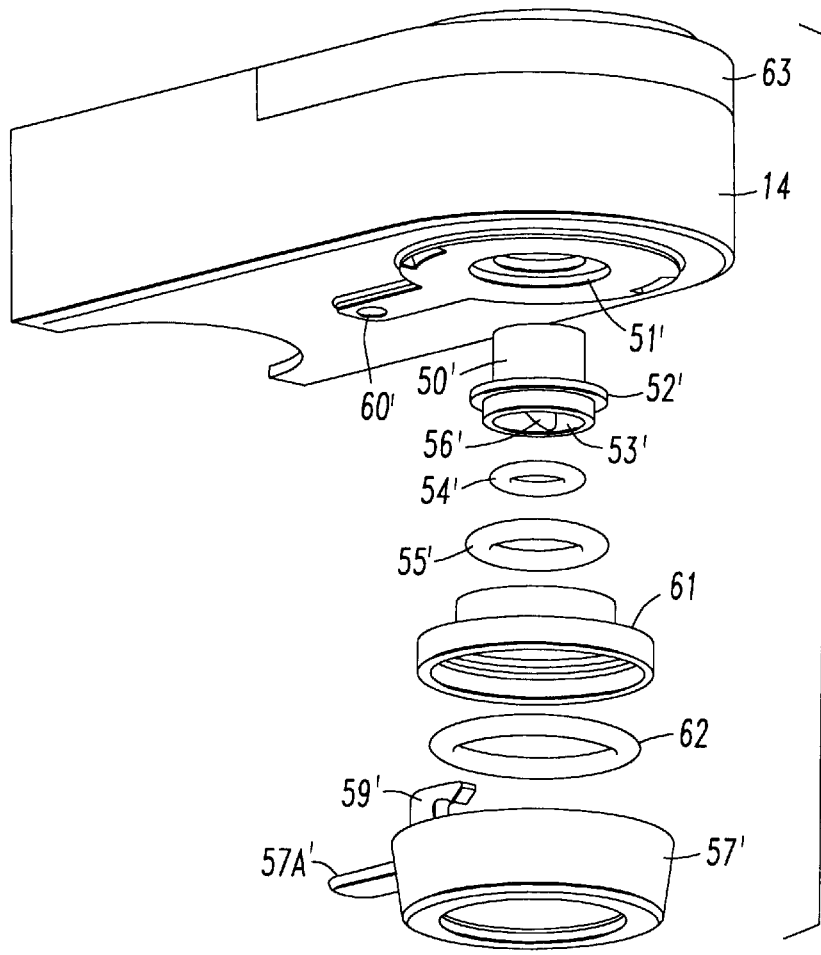
Figure 9:
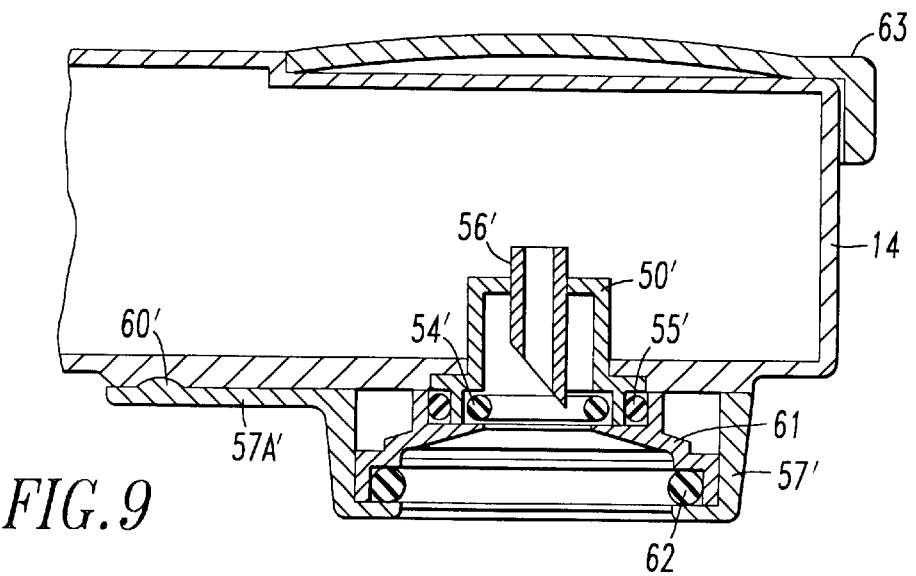
Figure 10:
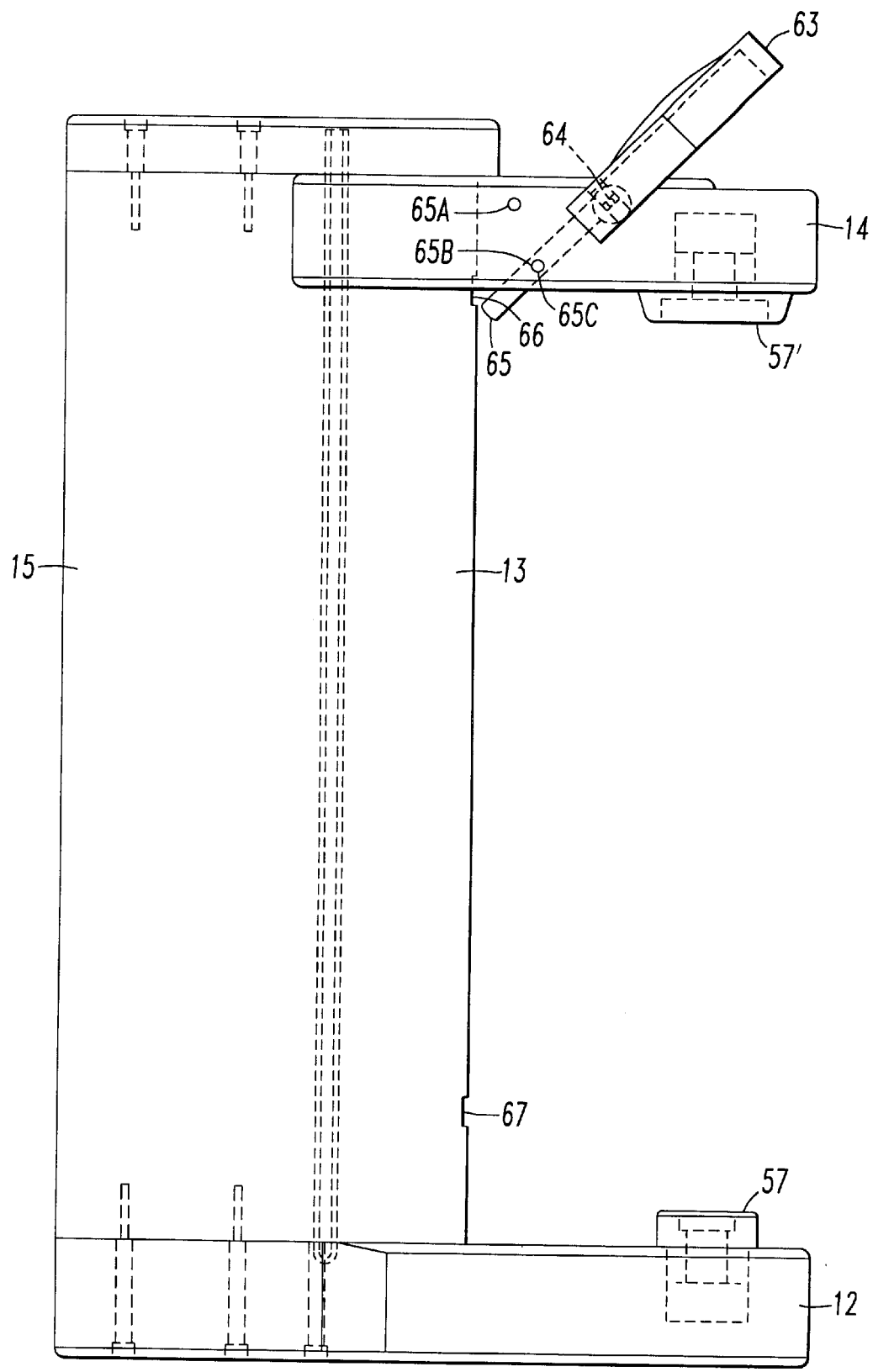
Figure 11:
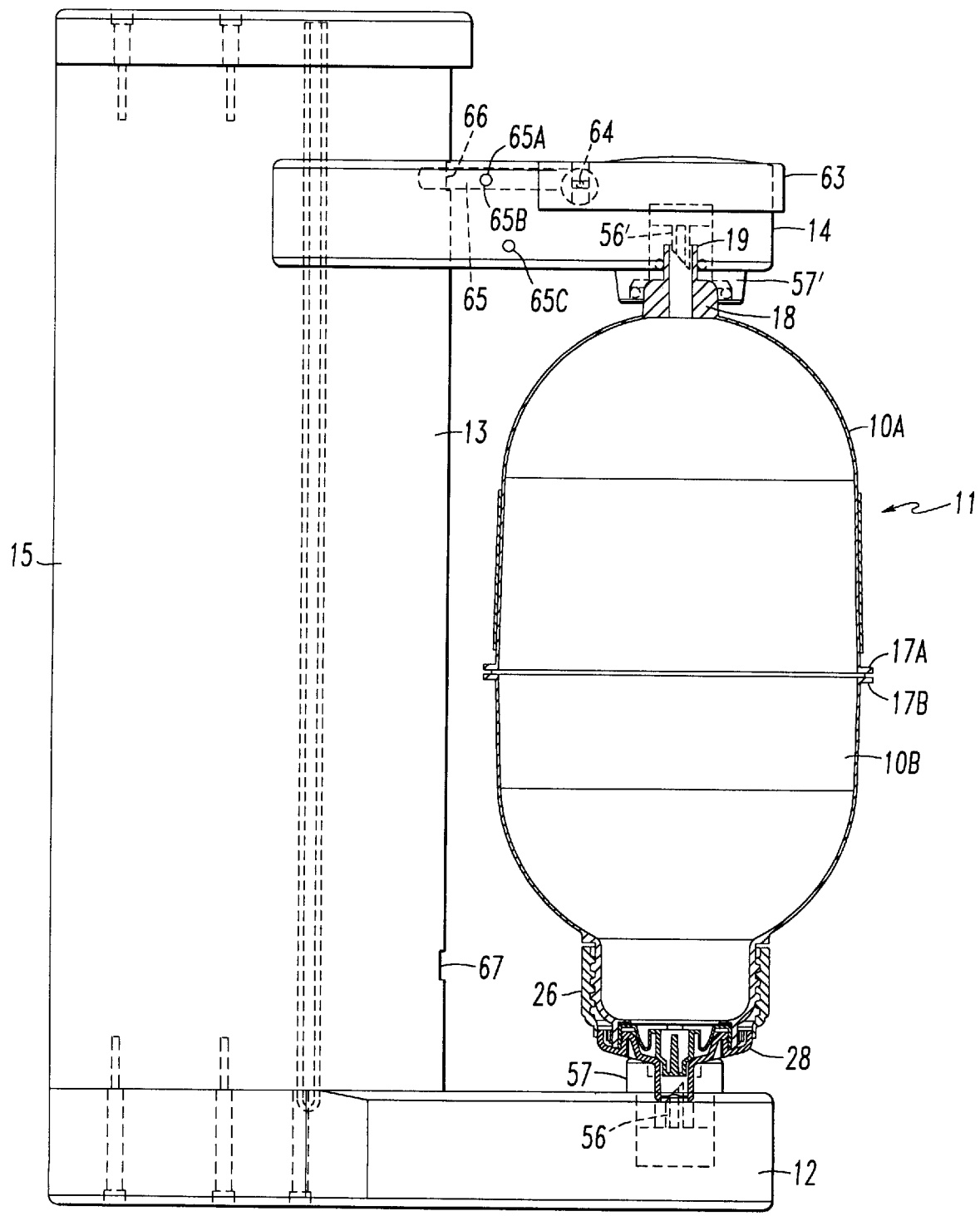
Figure 12:
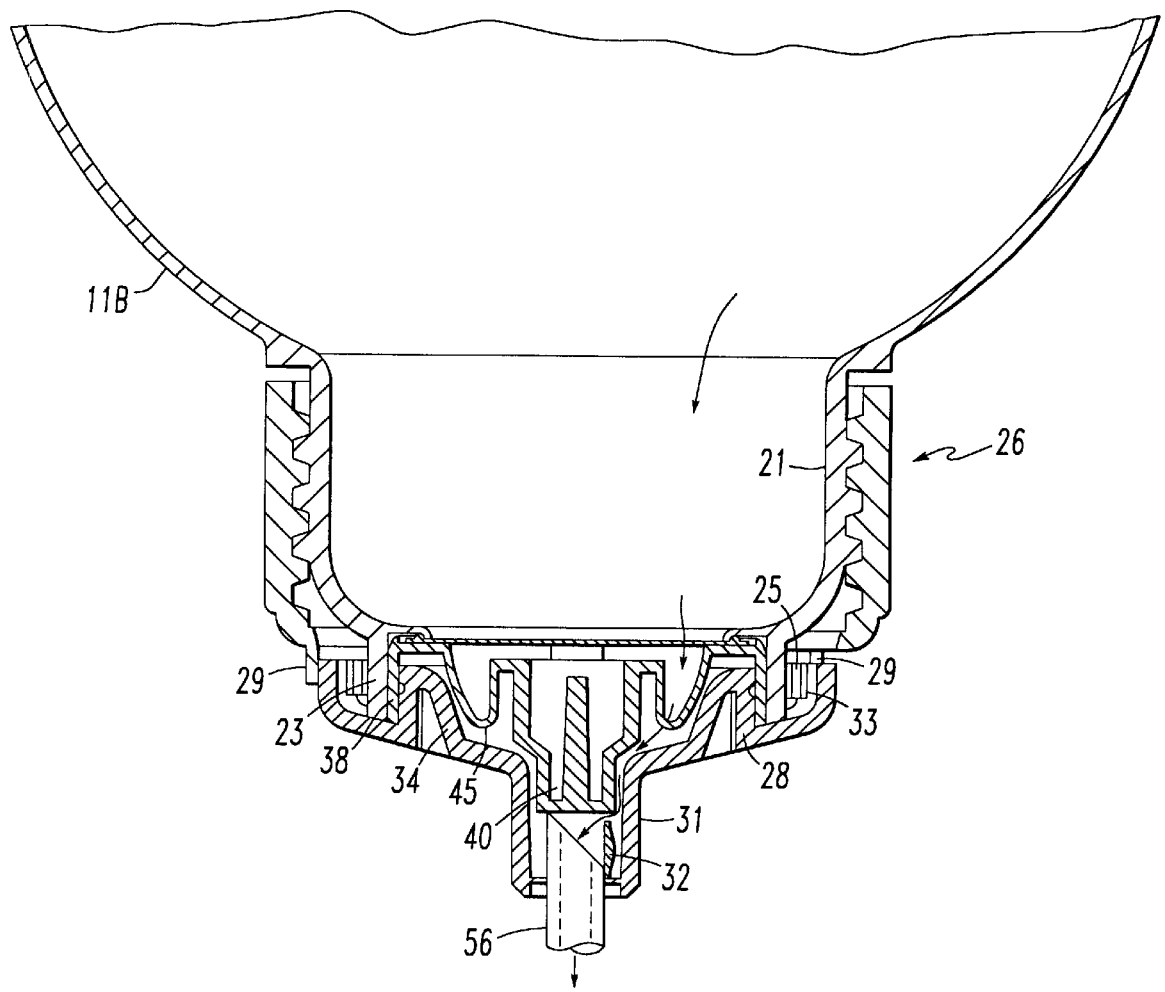
Figure 13:
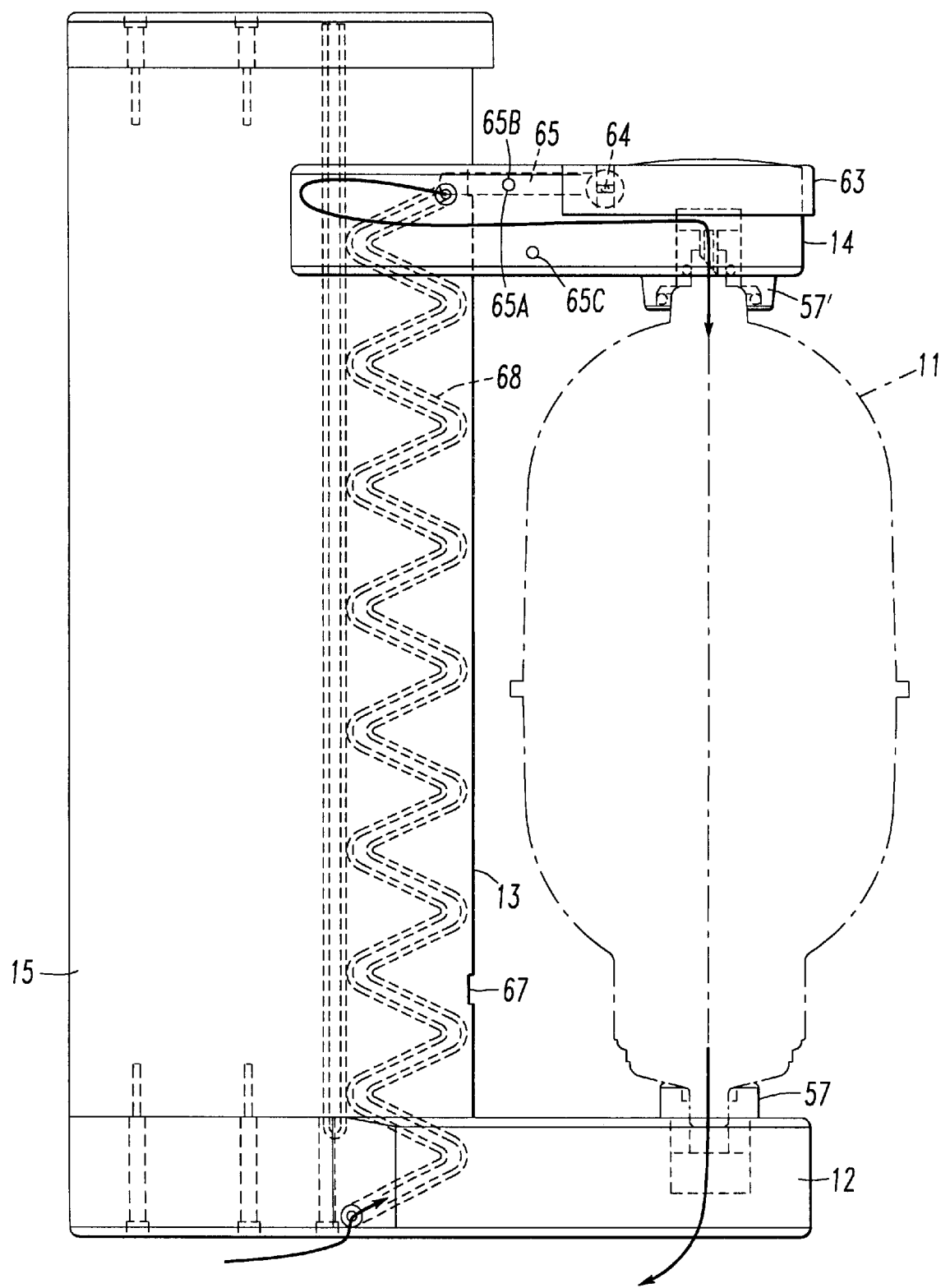
Figure 14:
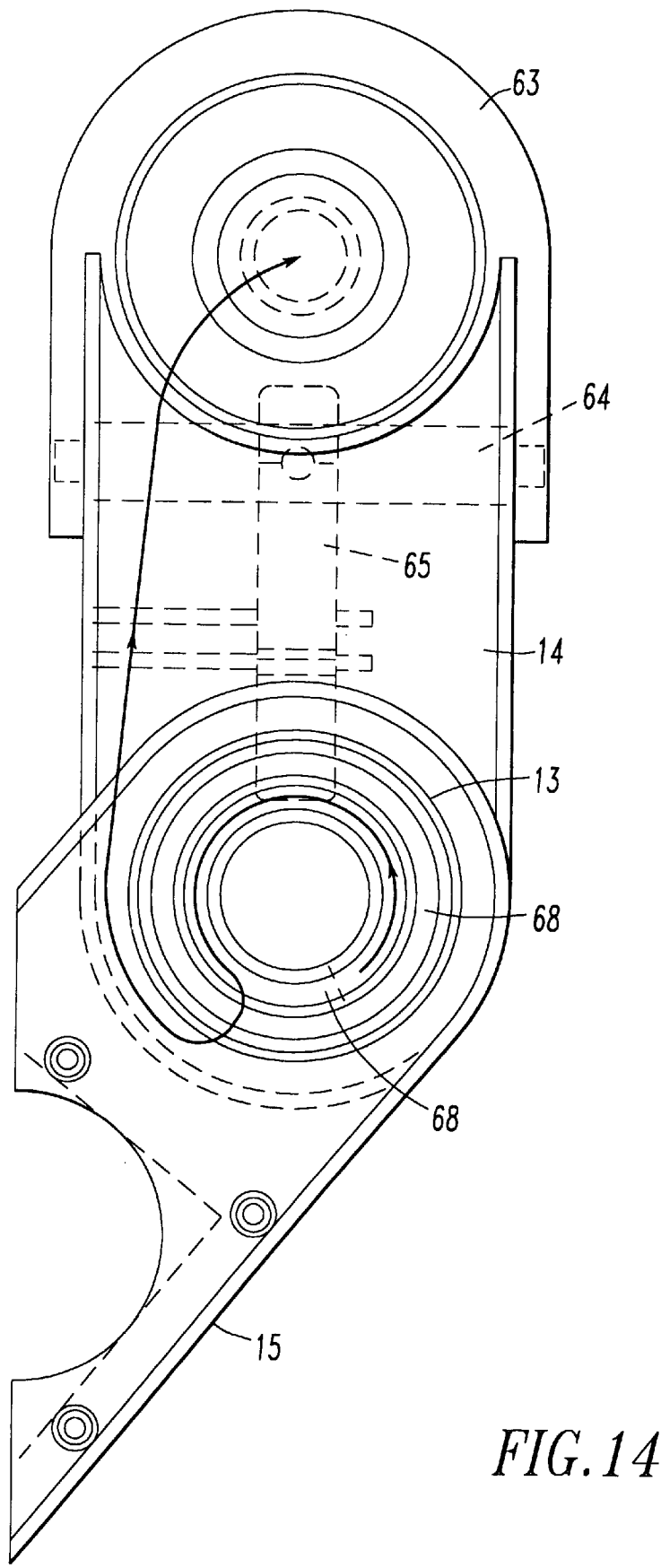
Figure 15:
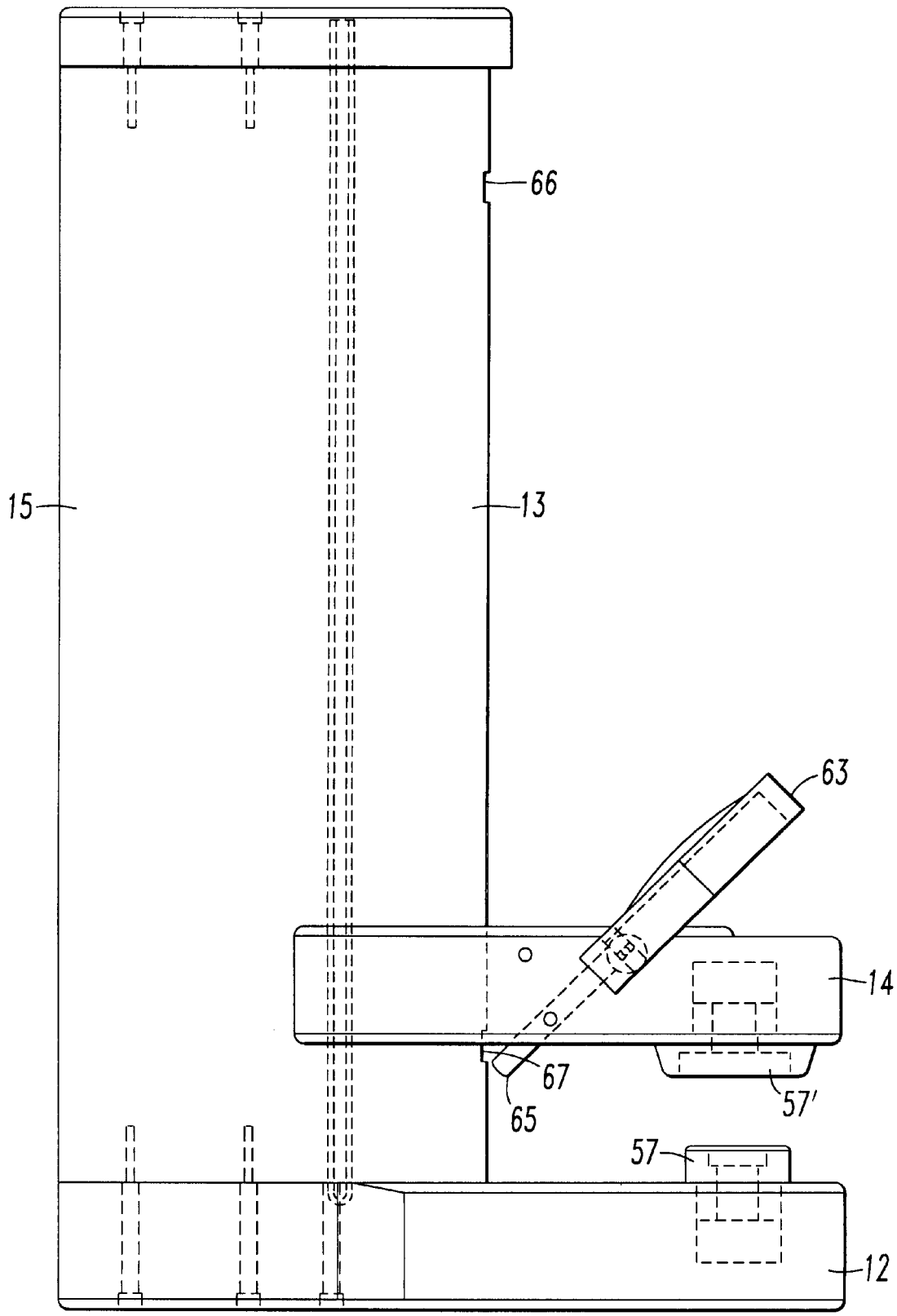
Figure 16:
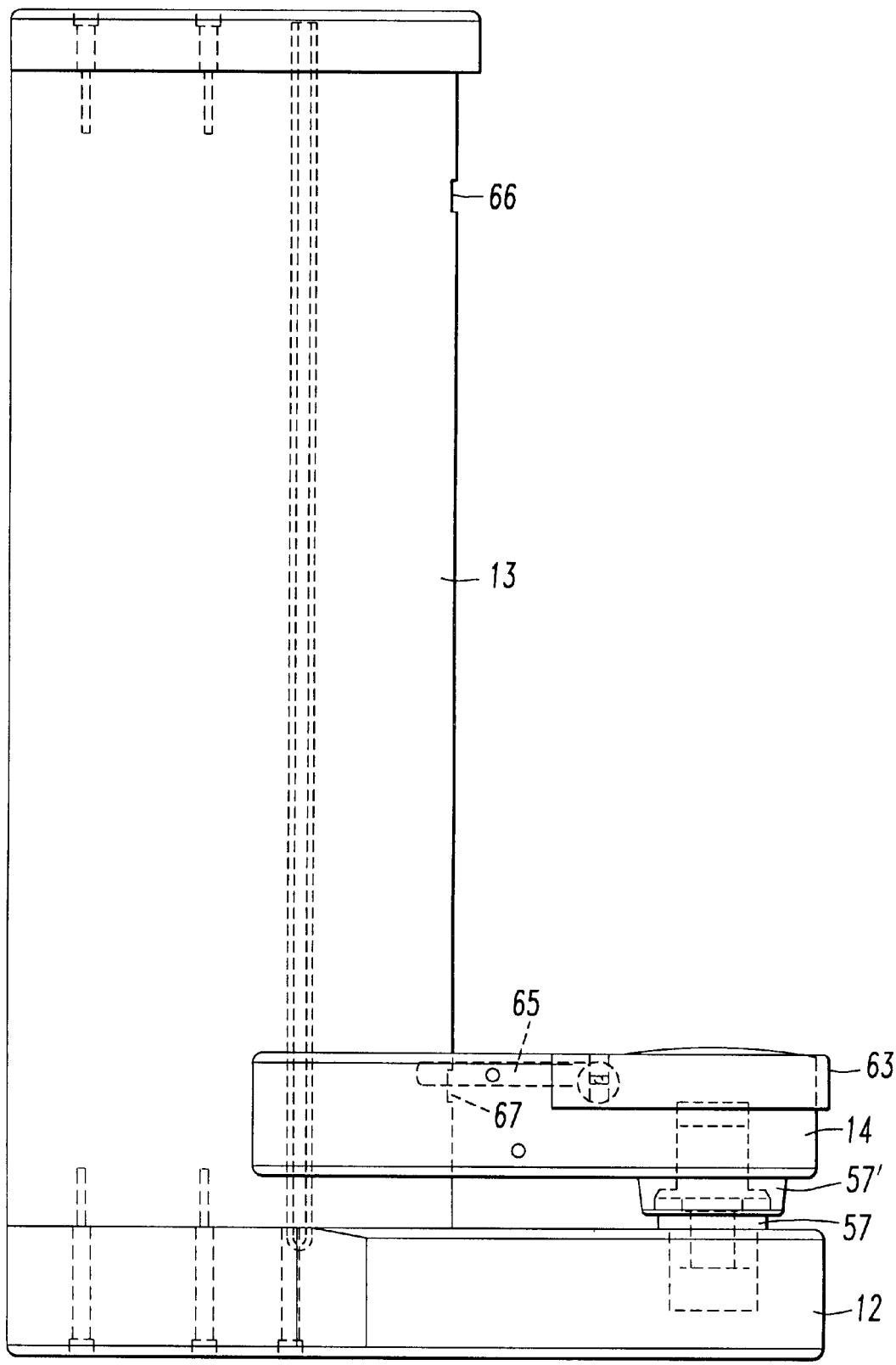
Figure 17:
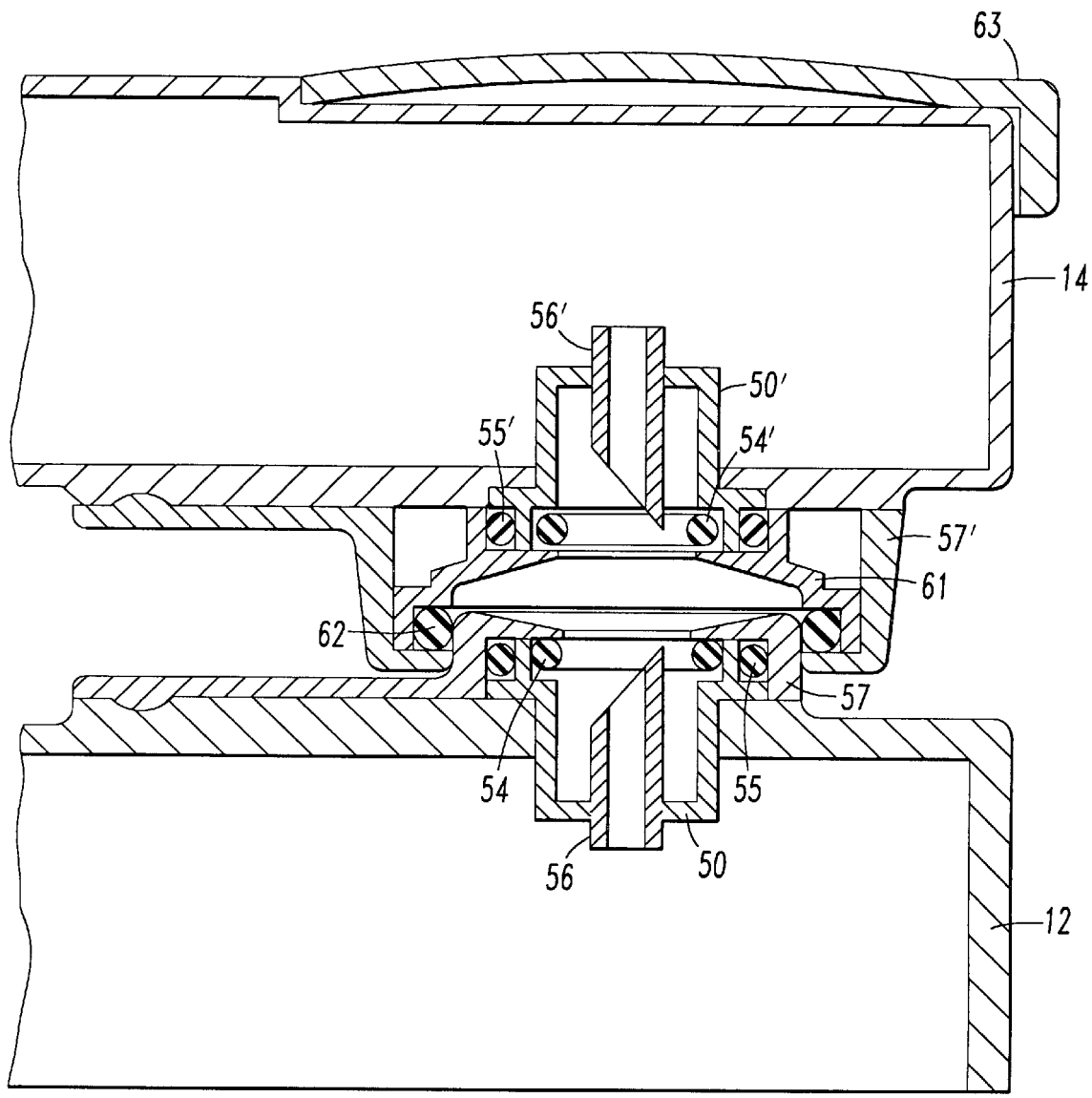
Figure 18:
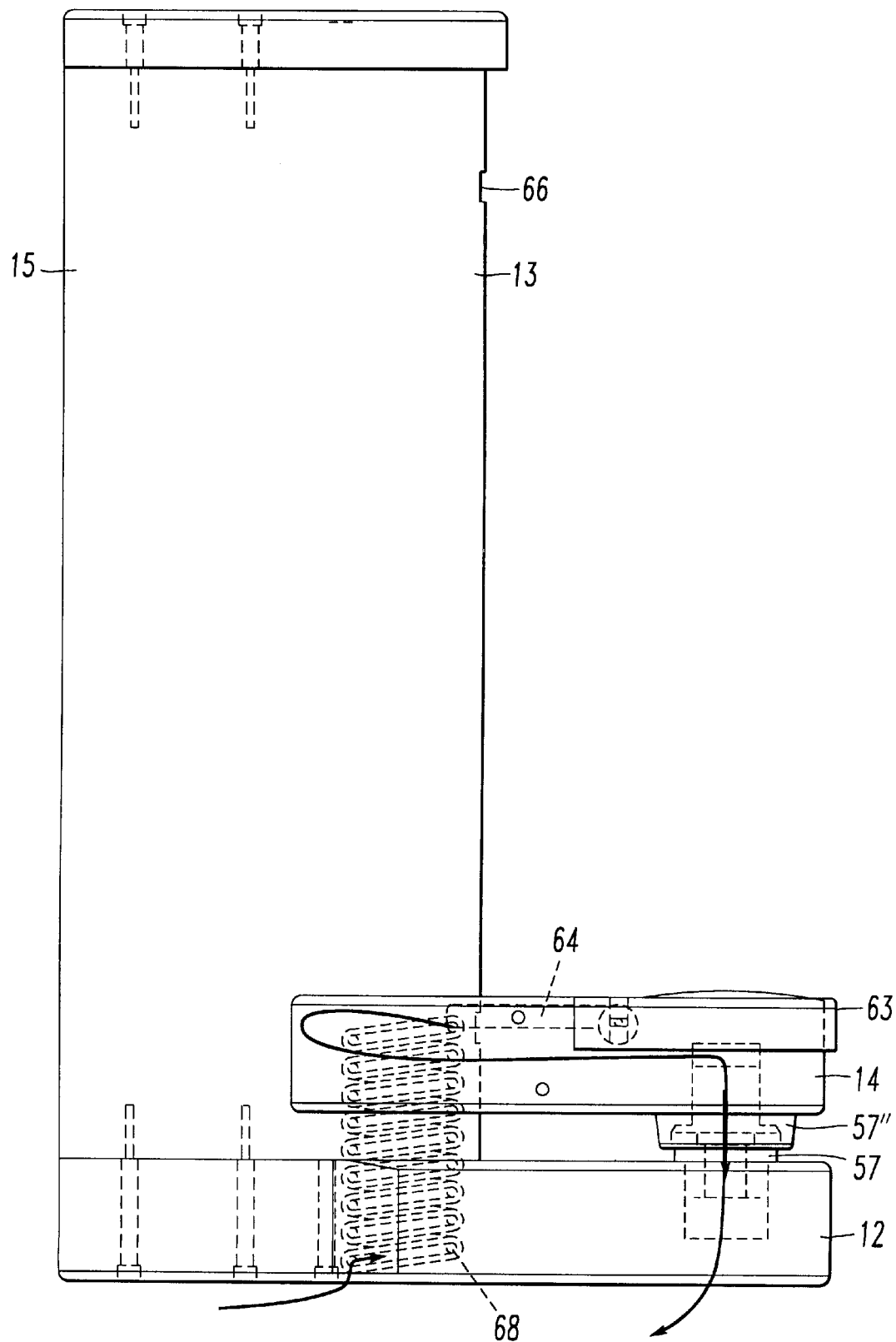

In order to explain the invention in more detail an illustrative embodiment will be described with reference to the accompanying drawings in which FIG. 1 is a perspective view of a dialysis machine with the device according to the invention, FIG. 2 is a side view of the powder cartridge mounted in the dialysis machine, FIG. 3 is an exploded perspective view of the powder cartridge, FIG. 4 is an enlarged axial cross-sectional view of the lower portion of the powder cartridge with neck and screw cap, a valve provided in the screw cap being in closed position, FIG. 5 is a perspective view of the holder for the powder cartridge, FIG. 6 is an exploded perspective view of the lower yaw of the holder, FIG. 7 is a vertical cross-sectional view of the lower yaw of the holder, FIG. 8 is an exploded perspective view of the upper yaw of the holder, FIG. 9 is a vertical cross-sectional view of the upper yaw of the holder, FIG. 10 is a side view of the holder without the powder cartridge, FIG. 11 is a side view of the holder with the powder cartridge mounted therein FIG. 12 is an axial cross-sectional view of the lower end of the powder cartridge similar to FIG. 4 but with the valve in a open position, FIG. 13 is a side view similar to FIG. 11 but without the powder cartridge, illustrating the liquid flow, FIG. 14 is a plan view of the holder and the upper yaw illustrating the water flow, FIG. 15 is a side view of the holder with the upper yaw displaced to a lower position, FIG. 16 is a side view of the holder with the yaws interengaged for performing a rinsing and disinfection cycle, FIG. 17 is an enlarged vertical cross-sectional view of the yaws in the position of FIG. 16, and FIG. 18 is a view similar to FIG. 16 disclosing the water flow during the rinsing cycle.

In FIG. 1 in the drawing there is disclosed a dialysis machine 10 which is supposed to be of the type DrakeWillock® system 1000™ and in the present case is set up to operate with preparation of dialysis liquid from a powder concentrate (sodium bicarbonate), which in an amount intended for one or more treatments is enclosed in a disposable cartridge 11. This cartridge is mounted to the machine between a stationary lower yaw 12 and a movable upper yaw 14 which can be displaced towards and away from the lower yaw on a tubular guide 13. Said guide is supported by an holder 15 which is mounted to a vertical mounting rail 16 provided externally on the machine. Means not shown in detail in FIG. 1 are provided for conducting water through the cartridge for dissolving the powder in the water as is known per se in connection with dialysis machines.

Cartridge 11, FIGS. 2 and 3, is cylindrical with semispherically domed end portions and is made up of two parts 11A and 11B of injection molded plastics, preferably polypropylene, which are interconnected by mirror welding at outwardly projecting circumferential flanges 17A and 17B, respectively. One part 11A, the upper part, which has a larger axial length than the other part 11B such that the joint between the parts at flanges 17A and 17B is not located midway of the cartridge forms a central circular hollow stud in the domed end, said stud comprising a portion 18 connecting to part 11A and having a larger diameter, and a portion 19 projecting therefrom and having a smaller diameter, the hollow stud thus formed communicating with the interior of the cartridge and being closed at the outer end thereof by means of a membrane 20 formed as an end wall on the stud.

The other part 11B of the cartridge forms in the domed end thereof a central circular neck 21 having an external screw thread 22. The neck joins a circular axially directed collar 23 which has internally a smooth cylindrical surface 24 and has externally a circumferential row of a saw teeth 25. A cap 26 having a grooved or knurled outside surface and internal screw threads 27 is dimensioned to be screwed onto the neck and has an end wall 28 which is connected with the rest of the cap by means of a number of shear webs 29 distributed over the circumference of the cap a small slit or cut 30 being provided between the end wall and the rest of the cap said slit or cut being bridged by the shear webs 29. The cap with end wall 28 and shear webs 29 is injection molded in one piece of plastics, preferably the same plastics as that the cartridge is made of, viz. polypropylene. End wall 28 forms a circular hollow stud 31 projecting centrally from said end wall said stud being closed in the outer end thereof by means of a membrane 32 forming an end wall of the stud.

End wall 28 has internally a circular row of saw teeth 33 which are, however, inclined in the opposite direction to teeth 25 on the neck. Moreover, end wall 28 forms an internal annular bulge 34 having an outwardly directed cylindrical surface 35. A valve element 36 is mounted on bulge 34 said valve element comprising a circular ring 37 with a cylindrical axially directed collar 38. This collar is so dimensioned that it fits on the inside thereof against surface 35, and it has on the inside an annular bead 39 which snaps into an annular groove in surface 35 when the valve element is mounted on bulge 34 in the correct position thereof. The valve element comprises also a valve member 40 which is cylindrical but at a conical portion 41 merges from a portion 42 having a larger diameter, into a portion 43 having a smaller diameter, said latter portion having an outside diameter which is smaller than the inside diameter of hollow stud 31 so that portion 43 can project into said stud, and terminates at an end wall 44 at the lower end of the valve member. At the other, upper end thereof the valve member is connected with ring 37 by means of four thin resiliently flexible arms 45 so that the valve member 40 can be moved axially in relation to the ring 37. When the valve element is mounted on bulge 34 the narrower portion 43 of valve member 40 projects into stud 31 the conical portion 41 resting under a certain pressure against the inside of end wall 28 where this joins stud 31, due to under the spring bias of arms 45 which are dimensioned to exert in this position of the valve member sufficient pressure on said member in order that the valve member will be kept in sealing engagement with end wall 28. Also valve element 36 preferably is injection molded of polypropylene.

A woven or injection molded filter net 46 also preferably of polypropylene is located in a recess in the upper surface of ring 37 and is connected to the ring by ultrasound welding.

After the cartridge thus constructed having been pressure tested for control of the tightness of the weld between flanges 17A and 17B an amount of powder (sodium bicarbonate) intended for a single dialysis treatment or several dialysis treatments is filled into the cartridge through neck 21, cap 26 then being screwed onto the neck until end wall 28 thereof engages the end surface of the neck. Then, the smooth inside surface 24 of collar 23 fits against the outside surface of collar 38 which has an annular bead 47 for sealing between collar 38 of the valve element and collar 23 of the neck. Collar 38 is clamped between surfaces 24 and 35 on collar 23 and bulge 34, respectively, securing necessary sealing between valve element 36 and neck 21 and between valve element 36 and bulge 34, respectively. Neck 21 has a radial flange 48 which at a flared edge portion 49 sealingly engages the upper surface of filter net 46 in the peripheral region thereof and also serves to locate valve element 36 in the cap when it is screwed on. Just before the cap is completely screwed on teeth 25 and 33 will interengage but these teeth shall be so orientated that they allow the cap to be screwed on, the teeth 33 of the cap rasping over teeth 25 on the neck without engaging therewith. The cartridge is then completely closed for storage and transport until it is connected to the dialysis machine. All parts of the cartridge including the net, valve element and cap, should be made of one and the same plastics and as mentioned above a suitable material is polypropylene.

The holder comprising yaws 12 and 14 in FIG. 1 in which the cartridge described shall be mounted will now be described with reference to FIGS. 5 to 11 and 13 to 18. The stationary yaw 12 is provided with a bushing 50 which is inserted into an aperture 51 in the yaw and at a shoulder formed by an outside flange 52 on the bushing rests on the upper surface of the yaw. In an enlarged portion 53 a gasket in the shape of an O-ring 54 is located, and on flange 52 a further gasket in the shape of an O-ring 55 is located. Inside bushing 50 there is provided a tube 56 which can be attached to the bushing or be integral therewith. The upper end of the tube is made tapering by being obliquely cut off similar to a cannula while the lower end of the tube is adapted to be connected to a hose. A lid 57 having a central opening 58 is provided over bushing 50 and is mounted to yaw 12 by means of bayonet coupling means 59 for engagement into matching slots 59A in the yaw. An arm 57A with a projection 57B on the lower side thereof is provided on lid 57, and when the lid has been located and the bayonet coupling has been engaged by turning the lid projection 57B is received in a depression 60 in the yaw. Arm 57A is sufficiently resilient so that projection 57B when the lid is being rotated in order to disengage the bayonet coupling can slide on the upper surface of the yaw and then snap into the depression 60 when the lid is locked in position. Lid 57 maintains O-rings 54 and 55 in position in the yaw.

The upper yaw has a similar arrangement; earlier described elements have been given corresponding reference numbers with the addition of a prime sign. In this case there is, however, also provided a ring 61 and a seal in the shape of an O-ring 62. Lid 57' which in this case has a larger diameter than lid 57 on the lower yaw keeps ring 61 pressed against the yaw while the ring in turn maintains bushing 50' in opening 51' and also maintains O-rings 54' and 55' in position. O-ring 62 located between ring 61 and lid 57' is received by ring 61 and is maintained in position by this ring and the lid.

On the upper yaw 14 an operating member 63 is provided which can be swung upwards from the position shown in FIGS. 5 to 8 about an horizontal shaft 64 to the position shown in FIG. 10. The operating member is rigidly connected with a lever 65 inside yaw 14. When the operating member 63 is in the position shown in FIGS. 5 and 8 the free end of lever 65 engages a notch 66 in guide 13; see FIG. 11. Then, yaw 14 is kept in the position shown in FIG. 11. The operating member is arrested in this position by means of a protrusion 65A on the yaw, which engages a depression 65B on arm 65. When the operating member 63 is swung upwards yaw 14 will initially be moved two cm or so upwards along guide 13 by means of lever 65 engaging notch 66 said notch 66 in guide 13 forming an abutment for the yaw to be raised. If the operating member 63 is swung further upwards to the position according to FIG. 10 wherein the operating member is arrested by another protrusion 65C on yaw 14 engaging depression 65B, lever 65 will be disengaged from notch 66 and yaw 14 can now be displaced freely downwards along guide 13. When yaw 14 has been displaced downwards towards the stationary yaw 12, FIG. 15, it will be in a lower position, FIG. 16, when the operating member 63 is folded down with lever 65 engaging a notch 67 in guide 13.

An helical hose 68, FIGS. 13 and 14, which is located in the tubular guide 13 is, at the ends thereof, anchored to the lower and the upper yaw 12 and 14, respectively, and communicates below with a water conduit (not shown) in the dialysis machine 10 and at the top with tube 56' in the upper yaw 14 for supply of water to said tube 46' while another hose (not shown) is connected to tube 56 in the lower yaw 12 to be connected to the dialysis machine at a position where concentrated sodium bicarbonate solution shall be supplied for use in the dialysis machine.

The cartridge 11 described filled with powder and closed by means of capsule 26 is mounted between yaws 12 and 14 as shown in FIG. 11 and indicated by dot-and-dash lines in FIG. 13 in the following manner.

The upper yaw 14 is displaced upwards two cm or so by the operating member 63 being swung upwards, FIG. 10, and with the upper yaw in this position cartridge 11 at stud 31 on screw cap 26 is passed through the central opening in lid 57 on the lower yaw 12 and into socket 50. O-ring 54 will seal around stud 31. The pointed end of tube 56 is moved against end wall 32 and sufficient pressure is exerted on the cartridge in order that this end wall will be penetrated and will yield. The end wall has a circular shear line in order to be folded upwards as a pivoted lid when tube 56 is pressed against the end wall as is indicated in FIG. 4 by dot-and-dash lines. Tube 56 has such length that when screw cap 26 engages lid 57 on the lower yaw 12 the tube engages valve member 40 and has lifted said member from the seat thereof on end wall 28 against the spring bias of arms 45. After this application of the lower end of the cartridge on the lower yaw 12 operating member 63 is pressed down towards the position disclosed in FIG. 11 the movable upper yaw 14 being moved downwards receiving portion 19 having the smaller diameter of the hollow stud in the upper end of cartridge 11, in bushing 50' in the upper yaw 14 O-ring 54' sealing around the stud. At the insertion the pointed end of the cannula-like tube 56' will penetrate end wall 20 of the hollow stud. Sealing ring 62 is not effective in this position because portion 18 having the larger diameter of the hollow stud in the upper end of the cartridge has a considerably smaller diameter than the central opening in lid 57' on the upper yaw 14. Now, the cartridge is mounted between tube 56' on the upper yaw 14 and tube 56 on the lower yaw 12 to conduct water through the cartridge for dissolving the powder enclosed therein into the water for the performance a dialysis treatment. The solution discharged from the cartridge is a concentrate which will be diluted with water in the machine to the concentration required for the treatment. The liquid flow is disclosed in FIG. 13 where cartridge 11 is indicated with dot-and-dash lines only. However, the arrows in FIG. 12 will show that the liquid from the cartridge flows through neck 21, further through filter net 46 to and through the passage defined by means of collars 23 and 38 the liquid passing between arms 45 then to pass between the raised valve member 40 and the valve seat formed by end wall 28 to the hollow stud 31 and from there into tube 56. Slit or cut 30 is located outside the liquid passage.

When the treatment (or treatments) have been completed the "used" cartridge shall be removed which is effected by displacement of the upper yaw 14 upwards two cm or so by the operating member 63 being swung upwards (FIG. 10). Tube 56' on the upper yaw then will be drawn out of the hollow stud 19 at the upper end of the cartridge which then can be lifted from the lower yaw 12 the screw cap 26 being withdrawn from tube 56 and valve member 40 being again pressed against the seat thereof on end wall 28 by arms 45. This is an important function of the cartridge described because remaining liquid in the cartridge cannot flow out from the lower end of the cartridge when the cartridge is removed from the dialysis machine as is the case with existing cartridges for use in dialysis machines. Escaping liquid would of course soil the lower yaw and parts of the dialysis machine located below said yaw, which is not very nice for the people who are handling the dialysis machine. Now, the cartridge can be taken to a sink or the like where the screw cap at the lower end of the cartridge is unscrewed for emptying the cartridge. Unscrewing which is prevented per se by the locking engagement between teeth 25 on neck 21 and teeth 33 on end wall 28 of screw cap 26 cannot take place unless the shear webs 29 between end wall 28 and the rest of the screw cap are broken with the consequence that end wall 28 with valve element 36 can fall off the rest of the cap. Only an initial turning of the cap at unscrewing is necessary in order that the end wall will come loose and a free passage thus will be opened for the liquid through the cap from the interior of the cartridge. It is thus not necessary to unscrew the cap completely. As far as end wall 28 tightly adheres to the neck due to the fact that snug fit between bulge 34 on the end wall and collar 38 on the valve unit may be necessary in order to obtain satisfactory sealing therebetween it may be necessary to pull the end wall from the neck by the fingers after the initial unscrewing of the cap. As soon as the end wall has come loose and has fallen or has been pulled off the cap cannot be used for reclosing the cartridge, and it is thus made impossible for the cartridge to be filled again with powder at the site of use with following risk of wrong dosage, filling of wrong powder, or contamination of the interior of the cartridge.

The cartridge must thus be discarded after having been used once but the material thereof just as the material of the screw cap including the end wall and the valve element can be recovered and can be collected for recovery in a particulary convenient manner if the two parts as has been mentioned for the preferred embodiment consist of one and the same material for example polypropylene.

After each dialysis treatment a rinsing and disinfection cycle is effected in the dialysis machine disinfection liquid being passed from one yaw to the other without passing through a cartridge mounted between them. In order to effect a rinsing and disinfection cycle the upper yaw 14 is moved to the lower position in which it is engaged with the lower yaw 12 in the manner described above. Operation member 63 is swung upwards, FIG. 10, so that arm 65 disengages the upper notch 66 in guide 13, the yaw is pushed downwards along the guide under compression of hose 68 to the position according to FIG. 15, and the operating member 63 is swung downwards to engage the lower notch 67 for engaging yaw 14 with yaw 12, FIGS. 16 to 18. Then, lid 57 on the lower yaw 12 is received by the central opening in lid 57' on the upper yaw 14, FIG. 17, lid 57 on the lower yaw 12 being dimensioned in such a way that the O-ring 62 on the upper yaw 14 seals against the outside of lid 57 as shown in FIG. 17. O-rings 54 and 54' have no sealing function, however, with the yaws in this position. When rinsing and disinfection liquid now is allowed to flow to the upper yaw 14 through hose 68 the flow circuit is short-circuited to the lower yaw 12 as indicated in FIG. 18. As will be seen from FIG. 17 O-rings 54 and 54' are exposed to the flowing liquid so that they will be overflown by liquid under the rinsing and disinfection cycle, which is important because these O-rings shall seal against the two end connections of the cartridge and this sealing can be jeopardized if there is precipitation or coating of bicarbonate on the O-rings. It is not necessary, however, to rinse O-ring 62 because it has no sealing function in connection with the dialysis procedure itself.

The O-rings can all easily be exchanged when necessary by lids 57 and 57', respectively, thanks to the bayonet coupling easily being removed from the associated yaw as is necessary in order to get access to the O-rings for exchange. Also bushings 50 and 50' with tube 56 and 56', respectively, for the same reason can be easily exchanged if this would be necessary due to the fact that the pointed end of the tube has become blunt after use for some time. The holder for the cartridge is thus well suited for maintenance and repair works.

The embodiment described can be modified within the scope of the claims. thus, the valve in the screwcap can be constructed in another manner.

For example, the valve unit can also include the seat for the valve member which in the embodiment shown is formed by end wall 28. the valve can be replaced by a membrane or by a member of elastic porous material having a slot penetrated by the pointed end of tube 56 and 56', respectively, and closing automatically when the tube is withdrawn again. The valve in the cap can also be constructed as a spring bias ball valve. The main thing is that the valve is of such construction that it will normally be held in closed position and will be adjusted to open position when the cartridge is mounted in the dialysis machine.

We claim:

1. A powder cartridge for a dialysis machine comprising an externally threaded neck, a screw cap applied to said neck, said neck including an end wall, a normally closed valve in said screw cap which can be adjusted to an open position by mounting the powder cartridge in the dialysis machine, means on said end wall and said neck, said means being mutually engaged when screwing the screw cap onto the neck to prevent unscrewing of the screw cap from the neck, and a break connection between said end wall and a remaining portion of the screw cap to allow unscrewing of the screw cap only under breaking of the break connection for separating the end wall therefrom.

2. A powder cartridge as in claim 1, wherein a free passage is established through the screw cap by separation of the end wall from the remaining portion of the screw cap.

3. A powder cartridge as in claim 2, wherein the valve and the end wall are constructed as a unit.

4. A powder cartridge as in claim 3, wherein the end wall forms a bulge and the valve is mounted against said bulge.

5. A powder cartridge as in claim 4, wherein the valve comprises a valve member and a seat formed by the end wall, said valve member being held resiliently engaged with said seat.

6. A powder cartridge as in claim 5, wherein the end wall forms a hollow stud and wherein the valve member engaging the seat partly projects onto the hollow stud and can be raised from the seat by means of an element introduced into the hollow stud.

7. A powder cartridge as in claim 5, wherein the valve comprises a ring mounted between the neck and the bulge and resiliently bending arms connecting the valve member with the ring.

8. A powder cartridge as in claim 1, wherein said means comprises teeth integral with the end wall and the neck, said teeth being constructed to rasp over each other when the screw cap is being screwed onto the neck and to interengage to prevent the screw cap from being unscrewed from the neck.

9. A powder cartridge as in claim 1, wherein said break connection comprises shear webs connecting the end wall with the remaining portion of the screw cap and further comprising an axial collar on the neck, said shear webs being located radially outside said collar and an annular bulge on the end wall, said collar being sealed against said bulge.

10. A powder cartridge as in claim 7, wherein an axial collar is formed on the neck and the ring is mounted between said axial collar and said bulge.

11. A powder cartridge as in claim 6, wherein the valve comprises a ring mounted between the neck and the bulge and resiliently bending arms connecting the valve member with the ring.

12. A powder cartridge as in claim 11, wherein an axial collar is formed on the neck and the ring is mounted between said axial collar and said bulge.

13. A powder cartridge as in claim 8, wherein the valve comprises a ring mounted between the neck and the bulge and resiliently bending arms connecting the valve member with the ring.

* * * * *